US00PP28003P3

(12) United States Plant Patent
de Wet

(10) Patent No.: US PP28,003 P3
(45) Date of Patent: May 9, 2017

(54) ***ALOE* PLANT NAMED 'ANDORA'**

(50) Latin Name: ***Aloe* hybrid**
Varietal Denomination: ANDora

(71) Applicant: Charles Andrew de Wet, Johannesburg (ZA)

(72) Inventor: Charles Andrew de Wet, Johannesburg (ZA)

( * ) Notice: Subject to any disclaimer, the term of this patent is extended or adjusted under 35 U.S.C. 154(b) by 0 days.

(21) Appl. No.: 14/998,688

(22) Filed: Feb. 2, 2016

(65) Prior Publication Data

US 2016/0249512 P1 Aug. 25, 2016

Related U.S. Application Data

(60) Provisional application No. 62/176,493, filed on Feb. 19, 2015.

(51) Int. Cl.
*A01H 5/00* (2006.01)

(52) U.S. Cl.
USPC ..... Plt./373

(58) Field of Classification Search
USPC ..... Plt./373, 372
CPC ..... A01H 5/02
See application file for complete search history.

*Primary Examiner* — Kent L Bell
(74) *Attorney, Agent, or Firm* — Penny J. Aguirre

(57) ABSTRACT

A new and distinct cultivar of *Aloe* plant named 'ANDora', characterized by light orange-colored flowers, light greyish-green colored foliage, moderately vigorous growth rate, and upright-compact growth habit, is disclosed.

1 Drawing Sheet

Latin name of genus and species of plant claimed: *Aloe* hybrid.

Variety denomination: 'ANDora'.

BACKGROUND OF THE INVENTION

The present invention relates to a new and distinct cultivar of *Aloe* of hybrid origin, botanically known as *Aloe* 'ANDora' and will be referred to hereafter by its cultivar name, 'ANDora'. 'ANDora' is a new cultivar of flowering *Aloe* grown for landscape and container use.

The new cultivar was derived from a controlled breeding program established by the Inventor at a nursery in Linbro Park, Republic of South Africa in 1973. The overall purpose of the breeding program is to make selections of hybrid *Aloe* with desirable horticultural characteristics to include improved vigor, flowering ability, and disease resistance. 'ANDora' was selected in the Inventor's trial bed in July 2007 as a single unique plant from amongst the seedlings derived from a cross made in July 2005 between complex hybrids in the Inventor's breeding program as the female parent and male parents. The female (seed) parent of the new cultivar is the proprietary *Aloe* hybrid breeding selection coded A(GMH), not patented, characterized by its light reddish-pink colored flowers, light greyish-green colored foliage, and vigorous, upright-compact growth habit. The male (pollen) parent of the new cultivar is the proprietary *Aloe* hybrid breeding selection uncoded, not patented, characterized by its light orange-colored flowers, light greyish-green colored foliage, and moderately vigorous, upright growth habit.

Asexual reproduction of the new cultivar by offshoots and in vitro propagation since July 2007 in Linbro Park, Republic of South Africa and Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'ANDora' as a new and distinct cultivar of *Aloe* plant:

1. Light orange-colored flowers;
2. Light greyish-green colored foliage;
3. Moderately vigorous growth rate; and
4. Upright-compact growth habit.

Plants of the new cultivar differ from its female parent, in having a different flower color. 'ANDora' differs from its male parent in having a shorter and more compact plant habit.

Of the many commercially available *Aloe* cultivars, the most similar in comparison to the new cultivar is Safari Sunrise 'X5', U.S. Plant Pat. No. 23,267. However, in side by side comparisons, plants of the new cultivar differ from plants of 'X5' in at least the following characteristics:

1. Plants of the new cultivar have a flower color different from plants of 'X5';
2. Plants of the new cultivar have larger flowers than plants of 'X5'; and
3. Plants of the new cultivar have longer and different colored pistils than plants of 'X5'.

In addition plants of the new cultivar can be compared to *Aloe* Hedgehog 'Andhopg', not patented. However, in side by side comparisons, plants of the new cultivar differ from plants of 'Andhopg' in at least the following characteristics:

1. Plants of the new cultivar have a flower color different from plants of 'Andhopg';
2. Plants of the new cultivar are taller than plants of 'Andhopg'; and 3. Plants of the new cultivar flower later in the season than plants of 'Andhopg'.

BRIEF DESCRIPTION OF THE PHOTOGRAPHS

The accompanying photograph show, as nearly true as it is reasonably possible to make the same in color illustrations of this type, typical flower and foliage characteristics of the new cultivar. Colors in the photograph may differ slightly from the color values cited in the detailed description, which accurately describes the colors of 'ANDora'. The plants were 18 months old and were grown in 1-gallon containers for 10 months in Arroyo Grande, Calif.

DETAILED BOTANICAL DESCRIPTION

Figure 1:
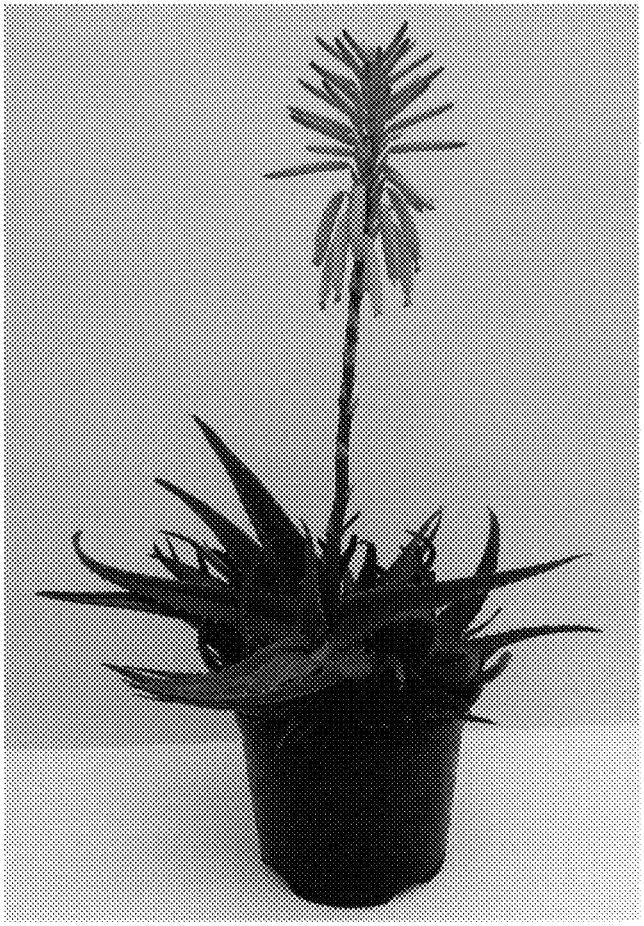
FIG. 1 illustrates a side view of the overall growth and flowering habit of 'ANDora'.
Figure 2:
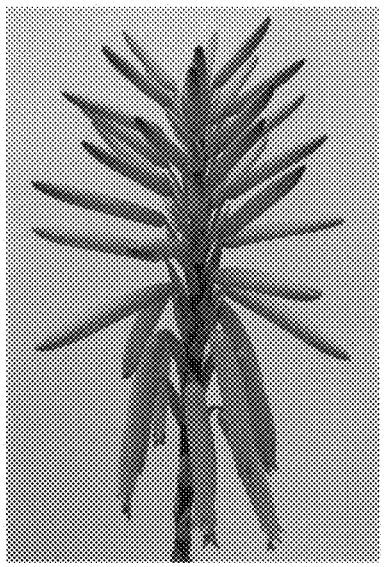
FIG. 2 illustrates a close-up view of an inflorescence of 'ANDora'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in November 2015 under natural light conditions in West Chicago, Ill. The following descriptions and measurements describe plants produced from in vitro plantlets from stock plants and grown in a poly-covered greenhouse without supplemental heating or cooling. Temperatures for this period ranged from an average daily high of 71° F. (22° C.) to an average daily low of 50° F. (10° C.). The plants were 18 months old and were grown in 1-gallon containers utilizing a soilless growth medium for 10 months in Arroyo Grande, Calif. No supplemental lighting was provided. Measurements and numerical values represent averages of typical plants.

Botanical classification: *Aloe* hybrid cultivar ANDora.

Parentage:

*Female parent*.—Proprietary *Aloe* hybrid breeding selection coded A(GMH), not patented.

*Male parent*.—Proprietary *Aloe* hybrid breeding selection uncoded, not patented.

Propagation:

*Type*.—Offshoots or in vitro propagules.

*Time required for root development*.—Between 7 to 21 days at an average air temperature of 15° C. to 25° C.

*Time required to develop flowering sized plants*.—9 to 12 months.

*Root description*.—Medium in thickness, fleshy, cream to brown in color.

*Rooting habit*.—Moderately freely branching, dense.

Plant description:

*Plant type*.—*Aloe* hybrid, monoecious, evergreen.

*Plant habit and general appearance*.—Clump forming, rosulate, succulent.

*Blooming habit*.—Blooms autumn to winter and erratically throughout the year in hardy zones.

*Growth rate*.—Moderately vigorous.

*Height and spread*.—Height from soil level to top of plant plane: Approximately 45.0 cm. Width: Approximately 29.0 cm.

*Hardiness*.—U.S.D.A. Zone 10a.

*Diseases and pests*.—No unique aspects concerning susceptibility or resistance.

*Growing conditions*.—Tolerant in a range of soils from humic to sandy to light clay, performs well in full to filtered sun.

*Stems*.—Appearance: Covered by leaf bases. Stem surface: Glabrous. Length: Approximately 7.0 cm. Width at base: Approximately 1.5 cm. Color: 155B.

Foliage description:

*General description*.—Form: Simple. Arrangement: Alternate.

*Leaves*.—Quantity: Approximately 13 per rosette as grown in a 1-gallon container. Shape: Narrowly sword-shaped, elongated. Appearance: Sulcate. Margin: Denticulate, teeth colored 145C. Apex: Tapering to a sharp point. Base: Decurrent. Venation pattern: Parallel. Length: Approximately 16.5 cm. Width: Approximately 3.0 cm. Depth: Approximately 1.0 cm at thickest point. Texture of upper and lower surfaces: Glabrous. Color of upper and lower surfaces: Closest to N138B, slightly glaucous.

Inflorescence description:

*General description*.—Type: Dense racemes of single flowers held on erect and strong scapes. Length: Approximately 12.5 cm. Width: Approximately 10.0 cm. Fragrance: None detected. Quantity: Approximately 40 flowers and buds per inflorescence, with 1 to 2 inflorescences as grown in a 1-gallon container. Lastingness on plant: Flowers open from base towards the apex, average of 5 days per flower, not persistent.

*Peduncles* (*scapes*).—Strength: Very strong. Shape: Cylindrical, slightly flattened. Length: Approximately 26.0 cm to base of inflorescence. Diameter: Approximately 7.0 mm. Texture: Glabrous. Color: Closest to a mixture of 144A with 137B.

*Peduncle bracts*.—Arrangement: Alternately along length of peduncle. Shape: Ovate. Apex: Apiculate. Base: Truncate. Length: Approximately 1.3 cm. Width at base: Approximately 1.0 cm. Texture of upper and lower surfaces: glabrous, papery. Color: Closest to N155D with streaks of 200B, occasionally an overlay of 137A at apex.

Flower description:

*General description*.—Type: Solitary, campanulate, not persistent.

*Flower buds just before opening*.—Shape: Cylindrical. Length: Approximately 4.0 cm. Diameter: Approximately 7.0 mm. Texture: Glabrous. Color: 25C to 25D with 137A at apex.

*Perianth*.—Length: Approximately 4.2 cm plus pistil and anthers extending outward approximately 7.0 mm. Diameter: Approximately 8.0 mm.

*Tepals*.—Quantity: 6, arranged in two whorls. Length: Approximately 4.2 cm. Width: Approximately 5.0 to 6.0 mm, lower 2.0 mm fused. Margin: Entire. Apex: Broadly acute. Base: Fused. Texture of lower (outer) and upper (inner) surfaces: Glabrous. Color of lower (outer) surface when first and fully open: Closest to 25D with 145D at apex. Color of upper (inner)

surface when first and fully open: Lighter than 25D with a tint of 145D at apex.

*Pedicels*.—Length: Approximately 2.0 cm. Diameter: Approximately 1.0 mm. Texture: Glabrous. Color: 145A.

*Reproductive organs*.—Androcoecium: Stamen quantity: 6 per flower, inserted at base of ovary. Stamen length: Approximately 4.9 cm. Filament length: Approximately 4.7 cm. Filament color: 145D. Anther shape: Bilobed, dorisfixed. Anther length: Approximately 3.0 mm. Anther color: N25A with 25A. Pollen amount: Moderate. Pollen color: 25C. Gynoecium: Pistil quantity: 1 per flower. Pistil length: Approximately 4.5 cm. Stigma shape: Capitate. Stigma length: Less than 1.0 mm. Stigma color: 145D. Style length: Approximately 3.8 cm. Style color: 145C. Ovary shape: Ovoid, superior. Ovary length: Approximately 7.0 mm. Ovary width: 2.0 mm. Color: 145A.

Seed and fruit production: Neither seed nor fruit production has been observed.

What is claimed is:

1. A new and distinct cultivar of *Aloe* plant named 'ANDora', substantially as herein illustrated and described.

* * * * *